(12) United States Patent
Banning et al.

(10) Patent No.: US 8,884,012 B1
(45) Date of Patent: Nov. 11, 2014

(54) DYE COMPOUND AND METHOD OF MAKING THE COMPOUND

(71) Applicant: Xerox Corporation, Norwalk, CT (US)

(72) Inventors: Jeffrey H. Banning, Hillsboro, OR (US); Bo Wu, Wilsonville, OR (US); Nathan Starr, Ashland, OR (US); Stephan V. Drappel, Toronto (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 13/975,837

(22) Filed: Aug. 26, 2013

(51) Int. Cl.
*C07D 239/70* (2006.01)

(52) U.S. Cl.
CPC .................................. *C07D 239/70* (2013.01)
USPC ......................................................... 544/249

(58) Field of Classification Search
CPC .................................................... C07D 239/70
USPC ......................................................... 544/249
See application file for complete search history.

(56) References Cited

U.S. PATENT DOCUMENTS

| | | | |
|---|---|---|---|
| 4,565,424 A * | 1/1986 | Huffman et al. | 349/165 |
| 5,380,635 A | 1/1995 | Gomez et al. | |
| 5,763,134 A | 6/1998 | Busman et al. | |
| 5,782,966 A | 7/1998 | Bui et al. | |
| 5,959,105 A * | 9/1999 | Harada et al. | 544/231 |
| 6,174,937 B1 | 1/2001 | Banning et al. | |
| 6,309,453 B1 | 10/2001 | Banning et al. | |
| 6,329,128 B1 | 12/2001 | Helland et al. | |
| 6,348,592 B1 | 2/2002 | Ramsden et al. | |
| 6,515,811 B2 | 2/2003 | Ikuhara et al. | |
| 6,605,416 B2 | 8/2003 | Busman et al. | |
| 2010/0071592 A1 | 3/2010 | Tian et al. | |
| 2012/0274700 A1 | 11/2012 | Belelie et al. | |

FOREIGN PATENT DOCUMENTS

| | | | | |
|---|---|---|---|---|
| EP | 1985667 A2 | 10/2008 | | |
| WO | WO 2013087631 | * | 6/2013 | A61K 8/49 |

OTHER PUBLICATIONS

Bello, et al., Near-infrared-absorbing squaraine dyes containing 2,3-dihydroperimidine terminal groups, Journal of the Chemical Society, Chemical Communications (5), 452-4 (1993).*
Umezawa, et al., Water-soluble NIR fluorescent probes based on squaraine and their application for protein labeling, Analytical Sciences, 24(2), 213-217 (2008).*
Banning et al., "Dye Compounds, Method of Making the Compounds and Ink Composition Employing the Compounds", U.S. Appl. No. 13/975,714, filed Aug. 26, 2013.
Banning et al., "Phase Change Inks Containing Wax-Soluble Near-Infrared Dyes", U.S. Appl. No. 13/975,933, filed Aug. 26, 2013.
Pfüller et al., "Sudan Black B: Chemical Structure and Histochemistry of the Blue Main Components*", Histochemistry 54, 1977, pp. 237-250.
Park et al., "The Novel Functional Chromophores Based on Squarylium Dyes", Bull. Korean Chem. Soc. vol. 26, No. 3, 2005, pp. 428-432.
Maeda et al., "Near-infrared Absorbing Squarylium Dyes with Linearly Extended Π-Conjugated Structure for Dye-sensitized Solar Cell Applications", American Chemical Society, 2011, Abstract Only, 1 page.
Author Unknown, Solvent Soluble Near Infrared Absorption Dye ADS830AT, American Dye Source, Inc., Product Bulletin, Sep. 2006, 1 page.
Author Unknown, Near Infrared Laser Dye for Printing Applications ADS775MI, American Dye Source, Inc., Product Bulletin, Nov. 2004, 1 page.
Author Unknown, Near Infrared Laser Dye for Printing Applications ADS775MP, American Dye Source, Inc., Product Bulletin, Oct. 2006, 1 page.
Author Unknown, Near Infrared Laser Dye for Printing Applications ADS775PI, American Dye Source, Inc., Product Bulletin, Nov. 2004, 1 page.
Author Unknown, Near Infrared Laser Dye for Printing Applications ADS775PP, American Dye Source, Inc., Product Bulletin, Oct. 2006, 1 page.
Author Unknown, Near Infrared Absorption and Fluorescent Dye ADS780HO, American Dye Source, Inc., Product Information, May 2001, 1 page.
Author Unknown, Solvent Soluble Near Infrared Dye ADS798SM, American Dye Source, Inc., Product Information, Jun. 2010, 1 page.
Author Unknown, Near Infrared Laser Dye for Printing Applications ADS800AT, American Dye Source, Inc., Product Bulletin, Oct. 2006, 1 page.
Author Unknown, Near Infrared Laser Dye for Printing Applications ADS815EI, American Dye Source, Inc., Product Bulletin, Oct. 2006, 1 page.
Beverina et al., "Squaraine Compounds: Tailored Design and Synthesis towards a Variety of Material Science Applications", Eur. J. Org. Chem., 2010, pp. 1207-1225.
Tatarets et al., Dicyanomethylene Squarylium Dyes Red and Near-infrared Fluorescent Probes for Proteins and Cells, PRLS_31, SETA BioMedicals, poster, 1 page.
Vitek et al., Aldrichimica acta, vol. 1, No. 2, 1968, published by the Aldrich Chemical Company, Inc., pp. 1-9.
Yagi et al., "Squaiylium Dyes and Related Compounds", Top Heterocycl Chem, Apr. 14, 2008, pp. 133-181.
Banning et al., "Colorant Compounds", U.S. Appl. No. 14/011,762, filed Aug. 28, 2013.
Banning et al., "Phase Change Inks", U.S. Appl. No. 14/011,763, filed Aug. 28, 2013.

* cited by examiner

*Primary Examiner* — Erich A Leeser
(74) *Attorney, Agent, or Firm* — MH2 Technology Law Group LLP

(57) ABSTRACT

A perimidine coupler of formula 1:

$$\text{(1)}$$

where R and R' are substituents independently selected from the group consisting of a hydrogen atom, $C_1$ to $C_4$ alkyl or a solubilizing moiety comprising a substituted or unsubstituted $C_{10}$ to $C_{70}$ hydrocarbyl group. At least one of R and R' is not a hydrogen atom or $C_1$ to $C_4$ alkyl. R" and R'" can be independently selected from the group consisting of a hydrogen atom, $C_1$ to $C_6$ alkyl groups and halogens.

19 Claims, No Drawings

DYE COMPOUND AND METHOD OF MAKING THE COMPOUND

DETAILED DESCRIPTION

1. Field of the Disclosure

The present disclosure is directed to wax soluble perimidine coupler compounds and method of making them.

2. Background

Perimidine couplers are employed as electron donor components of chromogens in the dye industry, and can be used in a wide variety of dyes. Examples of such chromogens include commercial dyes, such as Solvent Black 3 (Cl 26150) and Acetone Acid Blue (Cl 20540), both of which are found in the Colour Index.

Perimidine couplers are generally relatively strong electron donors. As such, they can be used to make dyes having a sufficient bathochromic shift so that their lamda max resides in the near infrared (NIR) region of the electromagnetic spectrum (e.g., at wavelengths of about 700 nm to about 1400 nm). Such dyes are known as NIR absorbing dyes.

However, commercial perimidine couplers possess dimethyl appendages (as they are prepared by condensation of 1,8-diaminonaphthalene and acetone). It is difficult to make such dyes soluble in non-polar environments, such as wax based compositions (e.g., wax based phase change hot melt ink compositions). Dyes that lack sufficient solubility can precipitate out of solution, aggregate and/or "bloom", meaning that the dye separates out of solution and goes to the surface. When dyes aggregate, colors can become less vibrant. The lack of solubility of commercial perimidines in wax based compositions can therefore reduce dye quality and/or limit their use in wax based formulations.

Therefore, wax soluble perimidine couplers would be a desirable advancement in the art.

SUMMARY

An embodiment of the present disclosure is directed to a perimidine coupler of formula 1:

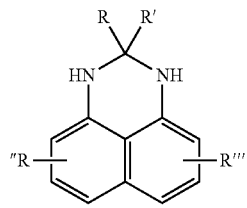

(1)

where R and R' are substituents independently selected from the group consisting of a hydrogen atom, $C_1$ to $C_4$ alkyl or a solubilizing moiety comprising a substituted or unsubstituted $C_{10}$ to $C_{70}$ hydrocarbyl group. At least one of R and R' is not a hydrogen atom or $C_1$ to $C_4$ alkyl. R" and R''' can be independently selected from the group consisting of a hydrogen atom, $C_1$ to $C_6$ alkyl groups and halogens.

Another embodiment of the present disclosure is directed to a method of making a perimidine coupler. The method comprises reacting 1,8-diaminonaphthalene and at least one carbonyl functionalized compound comprising a substituted or unsubstituted $C_{10}$ to $C_{70}$ hydrocarbyl group.

Still another method of the present disclosure is directed to a method of making a perimidine coupler. The method comprises reacting 1,8-diaminonaphthalene and a carbonyl functionalized compound to form a substituted intermediate perimidine structure. The substituted intermediate perimidine structure is reacted with a second compound to form a $C_{10}$ to $C_{70}$ hydrocarbyl substituted perimidine coupler, the second compound being selected from the group consisting of a $C_{10}$ to $C_{70}$ hydrocarbyl substituted acid, a $C_{10}$ to $C_{70}$ hydrocarbyl substituted isocyanate, a $C_{10}$ to $C_{70}$ hydrocarbyl substituted amine and a $C_{10}$ to $C_{70}$ hydrocarbyl substituted alcohol.

It is to be understood that both the foregoing general description and the following detailed description are exemplary and explanatory only and are not restrictive of the present teachings, as claimed.

DESCRIPTION OF THE EMBODIMENTS

Reference will now be made in detail to embodiments of the present teachings, examples of which are illustrated in the accompanying drawings. In the drawings, like reference numerals have been used throughout to designate identical elements. In the following description, reference is made to the accompanying drawing that forms a part thereof, and in which is shown by way of illustration a specific exemplary embodiment in which the present teachings may be practiced. The following description is, therefore, merely exemplary.

Dye Coupler Compounds

An embodiment of the present disclosure is directed to a perimidine coupler of formula 1:

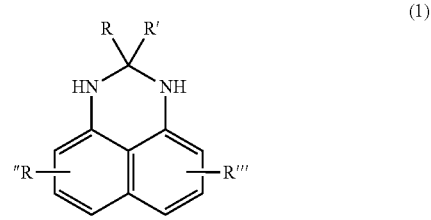

(1)

where R and R' are substituents independently selected from the group consisting of a hydrogen atom, $C_1$ to $C_4$ alkyl, such as methyl or ethyl, or a solubilizing moiety comprising a substituted or unsubstituted $C_{10}$ to $C_{70}$ hydrocarbyl group; wherein at least one of R and R' is not a hydrogen atom or $C_1$ to $C_4$ alkyl; and wherein R" and R''' can be independently selected from the group consisting of a hydrogen atom, $C_1$ to $C_6$ alkyl groups, nitro or halogens, such as chloro, fluoro or bromo groups. In an embodiment, R" and R''' are both hydrogen atoms.

Examples of the solubilizing moieties of R and R' can be $C_{10}$ to $C_{70}$ hydrocarbyl groups, such as linear, branched or cyclic alkyls; functional groups, such as carbamates, oxyalkyls, ethers, amides, amines or carboxylate groups, where the functional group includes a substituted or unsubstituted $C_{10}$ to $C_{70}$ hydrocarbyl tail; or polymers that include a $C_{10}$ to $C_{70}$ hydrocarbon backbone, such as carbonyl substituted polyethylene or polypropylene. The hydrocarbyl groups of the solubilizing moieties can potentially be substituted with any desired groups, including non-polar groups, such as alkyl side chains, or polar functional groups, such as carbonyl groups, as long as the substituents allow for the desired solubilizing effect of the hydrocarbyl to be realized.

In an embodiment, one or both of R and R' are carbamate esters. Examples of suitable carbamate ester substituents include groups of formula 2:

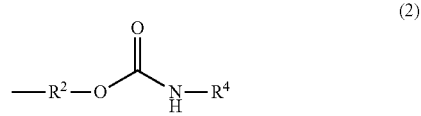

(2)

where $R^2$ is a $C_1$ to $C_4$ alkyl bridge, such as a methylene bridge or ethyl bridge, and $R^4$ is a $C_{12}$ to $C_{25}$ or $C_{50}$ alkyl. In an embodiment, $R^4$ is a $C_{15}$ to $C_{22}$ alkyl, such as n-hexadecyl, n-heptadecyl or n-octadecyl.

In an embodiment, one or both of R and R' are carboxylate esters. Examples of suitable carboxylate esters include substituents of formula 3:

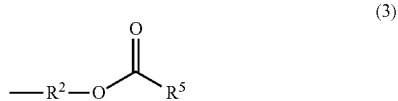

where $R^2$ is selected from the group consisting of a $C_1$ to $C_4$ alkyl bridge, such as a methylene bridge or ethyl bridge, and $R^5$ is a $C_{12}$ to $C_{25}$ or $C_{50}$ alkyl. In an embodiment, $R^5$ is a $C_{15}$ to $C_{22}$ alkyl, such as n-hexadecyl, n-heptadecyl or n-octadecyl.

In an embodiment, one of both of R and R' are linear, branched or cyclic $C_{10}$ to $C_{70}$ alkyls, such as $C_{12}$ to $C_{25}$ or $C_{50}$ alkyls, or $C_{16}$ to $C_{20}$ alkyls. In an embodiment, one or both of R and R' are selected from the group consisting of n-hexadecyl, n-heptadecyl and n-octadecyl.

In an embodiment, the solubilizing moiety of the perimidine couplers can include one or more substituted or unsubstituted aromatic rings, such as benzyl or phenyl containing groups, fused ring moieties, such as substituted naphthalenes, or aromatic heterocyclic ring containing groups. Examples of such aromatic ring substituted perimidine compounds are shown in the formulae below:

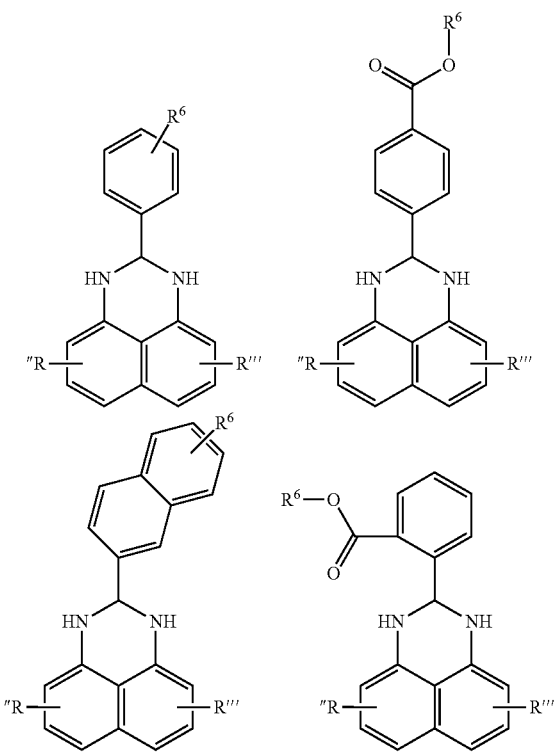

where $R^6$ can be a substituted or unsubstituted hydrocarbyl group, such as any of the solubilizing hydrocarbyl groups discussed herein. In an embodiment, the hydrocarbyl group is a $C_{10}$ to $C_{25}$ or $C_{50}$ alkyl. R" and R''' are defined as above. In an embodiment, R" and R''' are hydrogen atoms.

The perimidine couplers can be used as donors to form any type of donor-acceptor dyes, including NIR, UV and visible spectrum light absorbing dyes. Examples of NIR dyes formed using squaric acid are disclosed in co-pending U.S. patent application Ser. No. 13/975,714, filed Aug. 26, 2013, the disclosure of which is incorporated herein by reference in its entirety. In other applications, the wax soluble perimidine couplers can be combined with azo intermediates to make UV and visible absorbing dyes. The resulting dye compounds can be soluble in waxes based ink formulations or other compositions.

While compounds of the present disclosure include those of the structure of formula I above, it may be that other perimidine coupler compounds are also be formed by the synthesis processes of the present disclosure, as will be described below. It is intended that the present disclosure encompass any wax soluble perimidine couplers made by the processes described herein, including any couplers that are different than those of formula I. It is believed that the wax soluble perimidine couplers of the present disclosure will include at least one substituent comprising 10 or more carbons, such as a substituent selected from the group consisting of $C_{10}$ to $C_{70}$ alkyls, $C_{10}$ to $C_{70}$ carbamate esters, $C_{10}$ to $C_{70}$ carbamides or $C_{10}$ to $C_{70}$ carboxylate esters.

Synthesis of Perimidine Compounds

The present disclosure is also directed to methods of making perimidine coupler compounds. These methods result in perimidine couplers that comprise at least one solubilizing moiety, such as any of solubilizing moieties discussed herein. These methods will now be discussed in some detail.

One such method for making a wax soluble perimidine coupler comprises reacting 1,8-diaminonaphthalene and a wax tailed ketone or aldehyde, or other carbonyl substituted long chain hydrocarbyl compound. The carbonyl group reacts with the amine groups of the naphthalene compound to form a perimidine that includes the hydrocarbyl group as a solubilizing moiety.

Any suitable ketone or aldehyde that includes a sufficiently long hydrocarbyl tail to provide the desired solubilizing effect can be employed. In an embodiment, the ketone or aldehyde is a compound of formula 4:

where R and R' are independently selected from the group consisting of a hydrogen atom, $C_1$ to $C_4$ alkyl, such as methyl or ethyl or a substituted or unsubstituted $C_{10}$ to $C_{70}$ hydrocarbyl group, such as any of the alkyl groups having 10 or more carbons discussed herein, wherein at least one of R and R' is not a hydrogen atom or $C_1$ to $C_4$ alkyl. In an embodiment, the ketone is stearone.

The 1,8-diaminonaphthalene and ketone or aldehyde can be combined in any suitable manner, such as by mixing in a batch process. The reaction can occur neat or in a solvent. An example of a suitable solvent includes toluene. The mixture can be heated to provide the desired condensation reaction. In an embodiment, the reaction proceeds as follows, with water as a by-product:

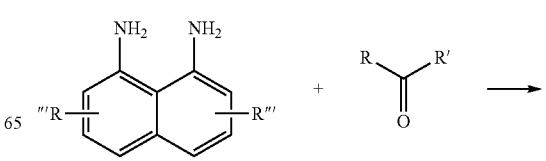

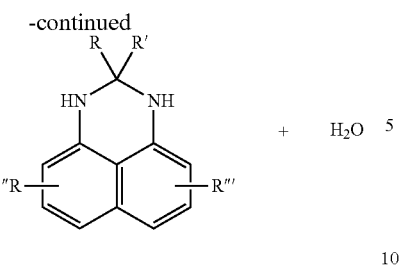

An example of another carbonyl substituted long chain hydrocarbyl compound that can be employed in place of the aldehyde or ketone in the above reaction is a copolymer of (a) carbon monoxide and (b) one or more short chain alkenes, such as the polymer of formula 5:

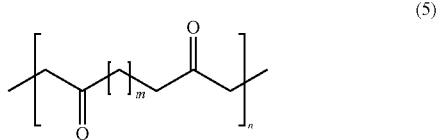

(5)

where m ranges from 1 to 8 and n is 3 or more, such as about 4 to about 25. Examples of suitable compounds of formula 5 include copolymers of carbon monoxide and at least one monomer chosen from ethylene and propylene.

In an alternative embodiment, a two-step synthesis route is employed to form the wax soluble perimidine couplers of the present disclosure. This alternative process comprises reacting 1,8-diaminonaphthalene and a hydroxyalkyl substituted carbonyl compound to form a hydroxyalkyl substituted perimidine. In the second step of the reaction, the hydroxyalkyl substituted perimidine can be reacted with a compound selected from the group consisting of a $C_{10}$ to $C_{70}$ hydrocarbyl substituted acid or a $C_{10}$ to $C_{70}$ hydrocarbyl substituted isocyanate to form a perimidine compound. In an embodiment, the hydrocarbyl substituted isocyanate is a phenyl isocyanate.

The hydroxyalkyl substituted carbonyl compound can be selected from the group consisting of ketones and aldehydes. For example, the hydroxyalkyl substituted carbonyl compound can be a compound of formula 6:

(6)

where $R^1$ and $R^2$ are independently selected from the group consisting of a hydrogen atom, $C_1$ to $C_4$ alkyl, such as methyl or ethyl, and $C_1$ to $C_4$ hydroxyalkyl, such as hydroxymethyl or hydroxyethyl, wherein at least one of $R^1$ and $R^2$ is not a hydrogen atom or $C_1$ to $C_4$ alkyl.

The 1,8-diaminonaphthalene and hydroxyalkyl substituted carbonyl compound can be combined in any suitable manner to form the hydroxyalkyl substituted perimidine, such as by mixing in a batch process. The reaction can be performed neat or in a solvent, while heating the mixture sufficiently to drive the condensation reaction.

After the hydroxyalkyl substituted perimidine compound is produced, it can be mixed with the desired acid or isocyanate to form a perimidine coupler. In an embodiment, the hydroxyalkyl substituted perimidine is reacted with a $C_{10}$ to $C_{70}$ hydrocarbyl substituted acid. An example of suitable acids include hydrocarbyl substituted carboxylic acid compounds of formula 7:

$$CH_3(CH_2)_n\text{---}CO_2H \qquad (7)$$

where n is an integer ranging from about 10 to about 70, such as about 12 to about 50. In another embodiment, n is an integer ranging from about 15 to about 18.

In an embodiment, the hydroxyalkyl substituted perimidine is reacted with a $C_{10}$ to $C_{70}$ hydrocarbyl substituted isocyanate. Examples of suitable isocyanates include compounds of formula (8):

$$CH_3(CH_2)_n\text{---}NCO \qquad (8)$$

where n is an integer ranging from about 10 to about 70, such as about 12 to about 50. In another embodiment, n is an integer ranging from about 15 to about 18.

Examples of isocyanate reactions to form carbamate substituted perimidines include the following:

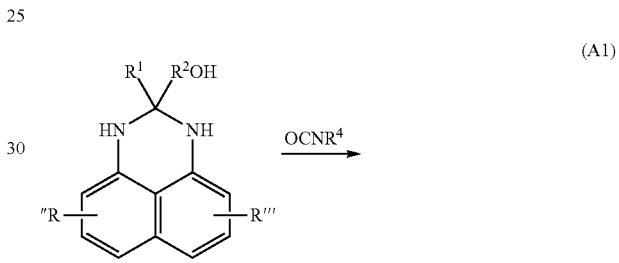

(A1)

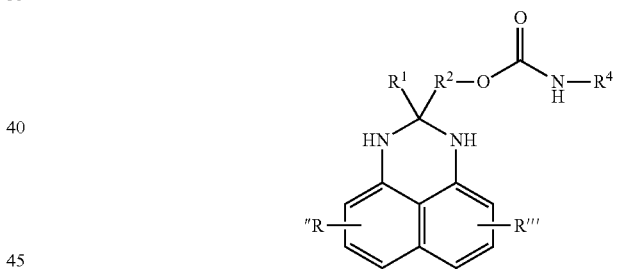

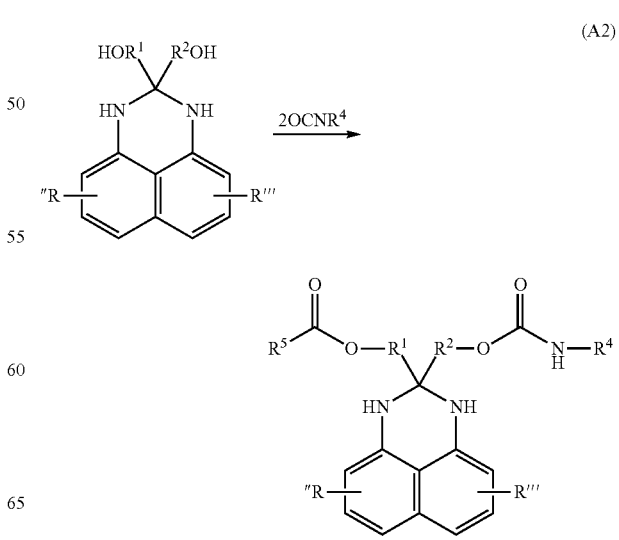

(A2)

Example reactions of the hydrocarbyl substituted carboxylic acid and hydroxyalkyl substituted perimidines discussed above include the following:

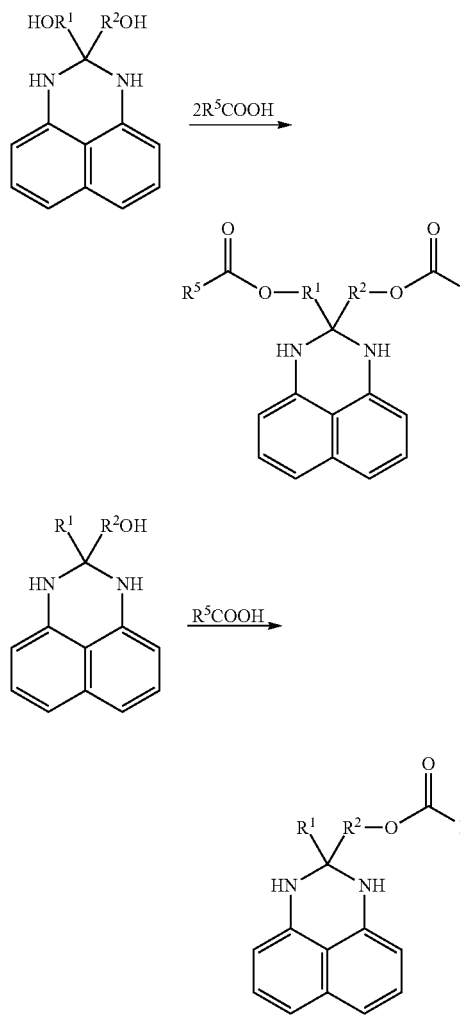

For the reactions A1 to A4 above, $R^1$, $R^2$, $R^4$, $R^5$, R" and R'" can be defined as set forth above for formulae 1, 2 and 3. In another embodiment, $R^1$ is selected from the group consisting of a hydrogen atom, methyl or ethyl; $R^2$ is chosen from a methylene bridge or ethyl bridge; R" and R'" are defined as above for formula 1; and $R^4$ and $R^5$ are $C_{15}$ to $C_{22}$ alkyls, such as n-heptadecyl or n-octadecyl. The reactions can occur in any suitable solvent. In some instances, it may be desirable to employ a catalyst and/or to use heat to drive the reaction, as would be understood by one of ordinary skill in the art.

Still other processes for forming the permidine couplers of the present disclosure can involve a transamidification or a transesterification pathway. In either case, a first step in the process can be to provide a short chain carboxylate substituted perimidine intermediate. One example of a pathway for forming such an intermediate comprises reacting a dialkyl mesoxalate with 1,8 diaminonaphthalene, as shown by reaction F1, below:

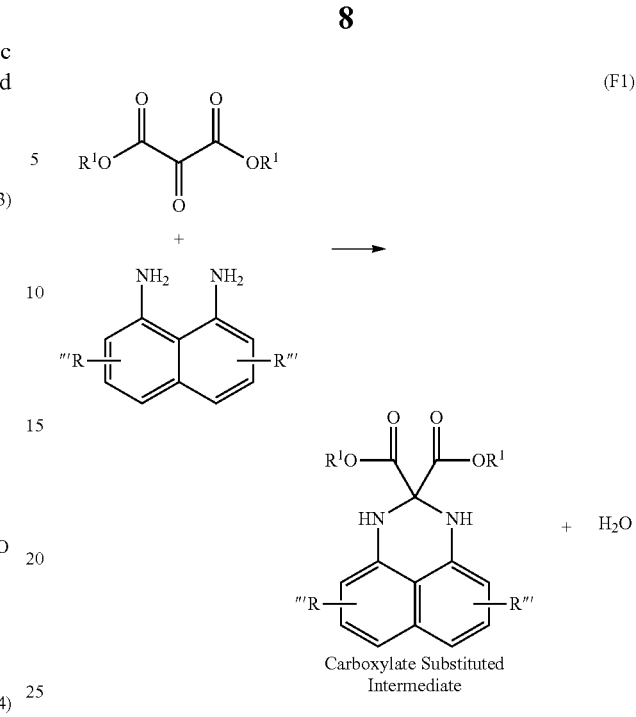

In the above reaction, $R^1$ is a $C_1$ to $C_4$ alkyl group, such as methyl or ethyl; and R" and R'" are defined as above with respect to the compounds of Formula 1. One example of a suitable dialkyl mesoxylate is diethyl mesoxalate, which is commercially available as Product No. M0866 from TCI-Chemicals of Portland, Oreg.

In an embodiment, transamidification of the intermediate can be carried out to replace the —$OR^1$ group with a —$NHR^8$ group to form an amide substituted perimidine coupler, as illustrated in reaction F2, below. The $R^8$ group can be a substituted or unsubstituted $C_{10}$ to $C_{70}$ hydrocarbyl, such as any of the alkyl groups having 10 or more carbons discussed herein.

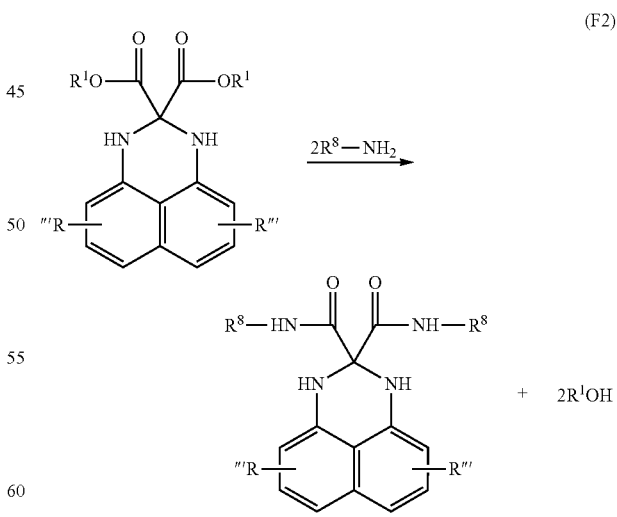

In another embodiment, transesterification of the intermediate formed in F1 can be carried out to replace the —$OR^1$ group with a —$OR^8$ group to form a carboxylate substituted perimidine coupler, as illustrated in reaction F3, below. The $R^8$ group can be a substituted or unsubstituted $C_{10}$ to $C_{70}$ hydrocarbyl, such as any of the alkyl groups having 10 or more carbons discussed herein.

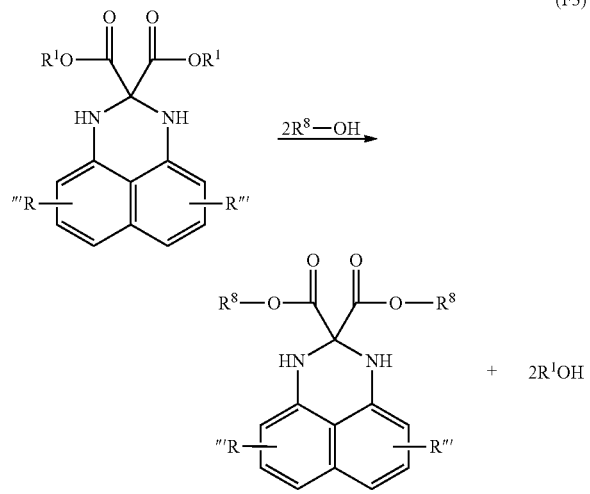

(F3)

EXAMPLES

Comparison Example

Preparation of 2,3-dihydro-2,2-dimethylperimidine

To a 100 mL flask with Teflon coated stir magnet was changed 20.9 g of 1,8-diaminonaphthalene (purified following the procedure of H.O. House, et al., J. Org. Chem. 1972, v37 n7, p. 1003) and a large excess of acetone (56 g) and allowed to stir at room temperature for about 65 hours. The acetone was then removed by a RT distillation process of blowing nitrogen across the flask until only the solid product remained. Thin Layer Chromatography (TLC—normal phase silica with toluene as the mobile phase) was then run on the reaction product and no starting materials (acetone or 1,8-diaminonaphthalene) were observed. An IR spectrum of the product was run and the peaks corresponded to the expected results which are believed to be the structure shown above (model compound).

Example 1

Preparing 2,3-dihydro-2,2-distearylperimidine

To a 1000 mL 3-neck 24/40 round bottom flask with stoppers on 2 of the necks, and a Dean-Stark trap with condenser on the center neck, and a Teflon coated stir magnet was charged 80 grams of stearone (commercial sample was employed, but see ORG SYN coll. vol 4 p 854 for preparation of stearone), 27.5 grams of 1,8-diaminonaphthalene (purified following the procedure of H.O. House, et al., J. Org. Chem. 1972, v37 n7, p. 1003)—representing a slight excess, 0.1 gram of PTSA and about 170 grams of toluene. The reaction vessel was placed in a 130° C. silicone oil bath and the reaction mixture allowed to reflux for about 16 hours. Water was collected with toluene in the Dean-Stark trap. Thin Layer Chromatography (TLC—normal phase silica with toluene as the mobile phase) was then run on the reaction product and no starting stearone was observed but some 1,8-diaminonaphthalene was observed as it was run in excess. The reaction mixture was poured into a 1 liter beaker with 400 mL of methanol and allowed to stir. The solid product was then collected via vacuum filtration (i.e., a Buchner funnel) and the solid collected was allowed to dry. Thin Layer Chromatography (TLC—normal phase silica with toluene as the mobile phase) was then run on the purified product and no starting materials—stearone or 1,8-diaminonaphthalene were observed. An IR spectrum of the product was run and the peaks corresponded to the expected results which are believed to be the structure shown below (2,3-dihydro-2,2-distearylperimidine).

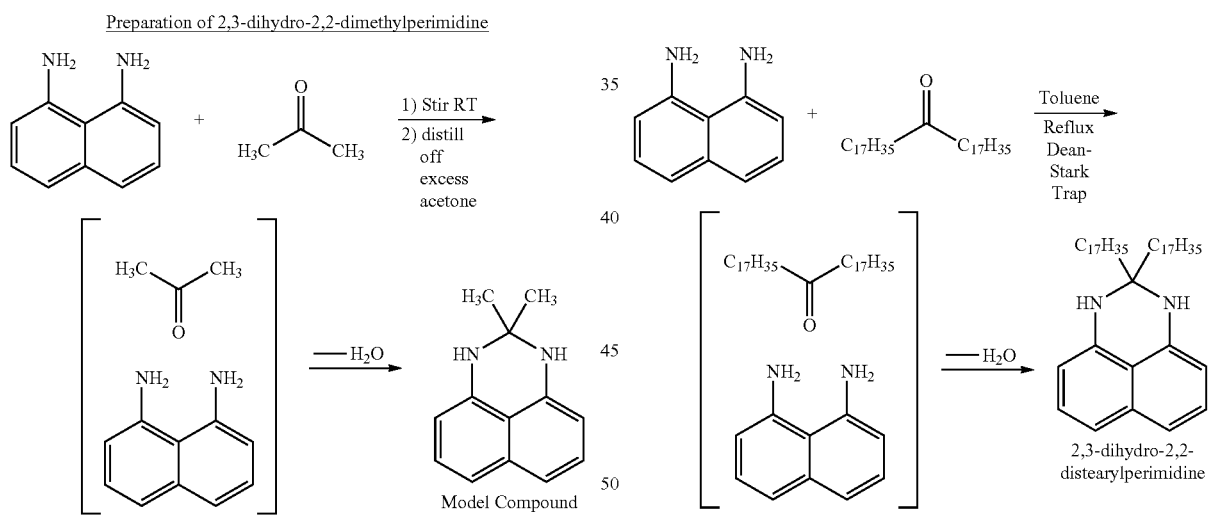

Example 2

Preparing 2,3-dihydro-2-methyl-2-hydroxyethylperimidine

To a 100 mL flask with Teflon coated stir magnet was added 33.4 grams of 4-hydroxy-2-butanone and 20 grams of 1,8-diamnonaphthalene. The reaction vessel was placed in a silicone oil bath at 70° C. and stirring initiated. After about 3 hours a sample was taken and Thin Layer Chromatography (TLC—normal phase silica with 90/10 MeOH/Toluene weight ratio as the mobile phase) was then run on the reaction product and no starting reactants were observed. The reaction product was poured into a 1 L beaker with 300 mL of DI water. The solids precipitated out and were collected via vacuum filtration (i.e., a Buchner funnel) and allowed to dry in a vacuum oven. An IR spectrum of the product was run and the peaks corresponded to the expected results which are believed to be the structure shown below (2,3-dihydro-2-methyl-2-hydroxyethylperimidine). About 24.9 g of product were obtained representing 86% yield.

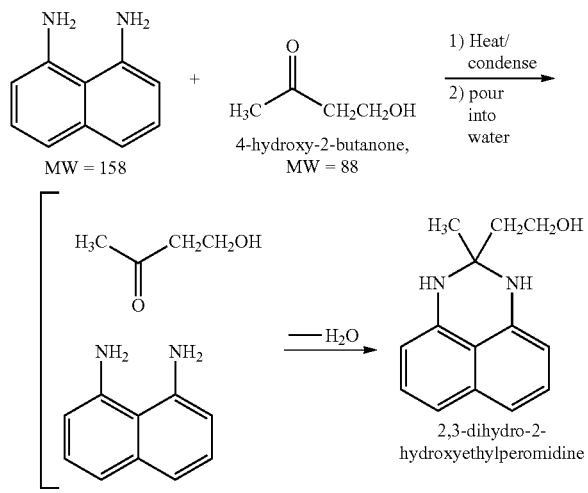

Example 3

Polymeric Perimidine

To a 1000 mL 3-neck 24/40 round bottom flask with stoppers on 2 of the necks, and a Dean-Stark trap with condenser on the center neck, and a Teflon coated stir magnet was charged 50 grams of ethylene-carbon-monoxide copolymer and 200 grams of xylene and the mixture was placed in a 140° C. silicone oil bath and stirred until the polymer was dissolved. About 5.0 grams of 1,8-diaminonaphthalene (with the polymeric carbonyls in molar excess) was added and heated-stirred till dissolved. The reaction mixture was then allowed to reflux for about 16 hours. Water was collected with toluene in the Dean-Stark trap. Thin Layer Chromatography (TLC—normal phase silica with 90/10 MeOH/Toluene weight ratio as the mobile phase) was then run on the reaction product and no starting 1,8-diaminonaphthalene was observed. The xylenes were distilled off and the molten product was poured into aluminum trays and allowed to solidify. An IR spectrum of the product was run and the peaks corresponded to the expected results which are believed to be the structure shown below (polymeric perimidine with not all of the carbonyls converted to perimidines).

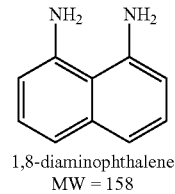

1,8-diaminophthalene
MW = 158

+

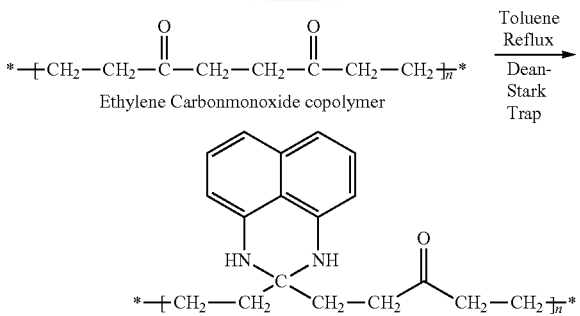

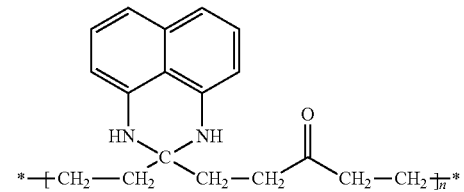

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the illustrated embodiment. Finally, "exemplary" indicates the description is used as an example, rather than implying that it is an ideal.

Other embodiments of the present teachings will be apparent to those skilled in the art from consideration of the specification and practice of the present teachings disclosed herein. It is intended that the specification and examples be considered as exemplary only, with a true scope and spirit of the present teachings being indicated by the following claims.

What is claimed is:
1. A perimidine coupler of formula 1:

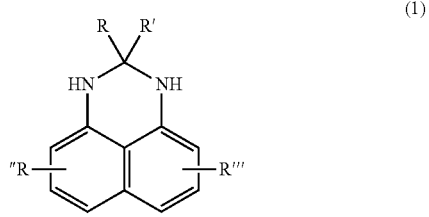

(1)

where R and R' are substituents independently selected from the group consisting of a hydrogen atom, $C_1$ to $C_4$ alkyl or a solubilizing moiety comprising a substituted or unsubstituted hydrocarbyl group; wherein at least one of R and R' is not a hydrogen atom or $C_1$ to $C_4$ alkyl; and wherein R" and R'" can be independently selected from the group consisting of a hydrogen atom, $C_1$ to $C_6$ alkyl groups and halogens, and wherein the R and R' solubilizing moieties comprising the substituted or unsubstituted hydrocarbyl group are selected from the group consisting of $C_{16}$ to $C_{70}$ linear, branched or cyclic alkyl groups, optionally, containing one or more heteroatoms; an oxyalkyl having a substituted or unsubstituted $C_{10}$ to $C_{70}$ hydrocarbyl tail; an ether having a substituted or unsubstituted $C_{10}$ to $C_{70}$ hydrocarbyl tail; a carbamate having a substituted or unsubstituted $C_{10}$ to $C_{70}$ hydrocarbyl tail; an amide having a substituted or unsubstituted $C_{10}$ to $C_{70}$ hydrocarbyl tail; an amine having a substituted or unsubstituted $C_{10}$ to $C_{70}$ hydrocarbyl tail; a carboxylate having a substituted or unsubstituted $C_{10}$ to $C_{70}$ hydrocarbyl tail; and polymers that include a $C_{10}$ to $C_{70}$ hydrocarbon backbone.

2. The compound of claim 1, wherein at east one of R and R' is a substituent of formula 2:

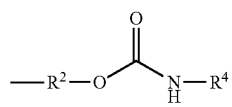

(2)

where $R^2$ is selected from the group consisting of a methylene and an ethyl bridge and $R^4$ is a $C_{12}$ to $C_{50}$ alkyl.

3. The compound of claim 2, wherein $R^2$ is methylene and $R^4$ is selected from the group consisting of n-hexadecyl, n-heptadecyl and n-octadecyl.

4. The compound of claim 1, wherein at least one of R and R' is a substituent of formula 3:

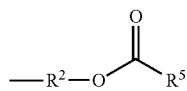

(3)

where $R^2$ is selected from the group consisting of a methylene and an ethyl bridge and $R^5$ is a $C_{12}$ to $C_{50}$ alkyl.

5. The compound of claim 4, wherein $R^2$ is methylene and $R^5$ is selected from the group consisting of n-hexadecyl, n-heptadecyl and n-octadecyl.

6. The compound of claim 1, wherein both of R and R' are $C_{12}$ to $C_{50}$ alkyls.

7. The compound of claim 1, wherein R and R' are selected from the group consisting of n-hexadecyl, n-heptadecyl and n-octadecyl.

8. A method of making the perimidine coupler of claim 1, the method comprising reacting 1,8-diaminonaphthalene and at least one carbonyl functionalized compound comprising a substituted or unsubstituted $C_{10}$ to $C_{70}$ hydrocarbyl group.

9. The method of claim 8, wherein the carbonyl functionalized compound is a compound of formula 4:

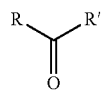

(4)

where R and R' are independently selected from the group consisting of a hydrogen atom, $C_1$ to $C_4$ alkyls or $C_{10}$ to $C_{70}$ alkyls, wherein at least one of R and R' is not a hydrogen atom or $C_1$ to $C_4$ alkyl.

10. The method of claim 8, wherein the carbonyl functionalized compound is stearone.

11. A perimidine coupler made by the method of claim 8, the perimidine coupler comprising at least one substituent selected from the group consisting of linear, branched or cyclic $C_{10}$ to $C_{70}$ alkyl groups optionally containing one or more heteroatoms.

12. A method of making the perimidine coupler of claim 1, the method comprising:
reacting 1,8-diaminonaphthalene and a carbonyl functionalized compound to form a substituted intermediate perimidine structure; and
reacting the substituted intermediate perimidine structure with a second compound to form a $C_{10}$ to $C_{70}$ hydrocarbyl substituted perimidine coupler, the second compound being selected from the group consisting of a $C_{10}$ to $C_{70}$ hydrocarbyl substituted acid, a $C_{10}$ to $C_{70}$ hydrocarbyl substituted isocyanate, a $C_{10}$ to $C_{70}$ hydrocarbyl substituted amine and a $C_{10}$ to $C_{70}$ hydrocarbyl substituted alcohol.

13. The method of claim 12, wherein the carbonyl functionalized compound is a hydroxyalkyl substituted carbonyl compound and the substituted intermediate perimidine structure is a hydroxyalkyl substituted perimidine; and
the second compound is selected from the group consisting of a $C_{10}$ to $C_{70}$ hydrocarbyl substituted acid and a $C_{10}$ to $C_{70}$ hydrocarbyl substituted isocyanate.

14. The method of claim 13, wherein the hydroxyalkyl substituted carbonyl compound is a compound of formula 6:

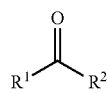

(6)

where $R^1$ and $R^2$ are independently selected from the group consisting of a hydrogen atom, $C^1$ to $C^4$ alkyl, hydroxymethyl and hydroxyethyl, wherein at least one of $R^1$ and $R^2$ is not a hydrogen atom or $C^1$ to $C^4$ alkyl.

15. The method of claim 14, wherein the hydroxyalkyl substituted perimidine is reacted with the hydrocarbyl substituted acid, the acid being a compound of formula 7:

$$CH_3(CH_2)_n\text{---}CO_2H \qquad (7)$$

where n is an integer ranging from 12 to 50.

16. The method of claim 15, wherein n is in integer ranging from 15 to 25.

17. The method of claim 14, wherein the hydroxyalkyl substituted perimidine is reacted with the hydrocarbyl substituted isocyanate, the isocyanate being a compound of formula (8):

$$CH_3(CH_2)_n\text{---}NCO \qquad (8)$$

where n is an integer ranging from 10 to 50.

18. The method of claim 17, wherein n is in integer ranging from 12 to 20.

19. A wax soluble perimidine coupler made by the method of claim 12, the perimidine coupler comprising at least one substituent selected from the group consisting of $C_{10}$ to $C_{70}$ carbamate esters, $C_{10}$ to $C_{70}$ carboxylate esters and $C_{10}$ to $C_{70}$ amides.

* * * * *